United States Patent
Chhabada et al.

(10) Patent No.: US 7,482,471 B2
(45) Date of Patent: Jan. 27, 2009

(54) PROCESS FOR PREPARATION OF 1-[9H-CARBAZOL-4-YLOXY]-3-[{2-(2-(-METHOXY)PHENOXY)-ETHYL}-AMINO]-PROPAN-2-OL

(75) Inventors: Vijay Chhangamal Chhabada, Akota (IN); Rajeev Budhdev Rehani, Akota (IN); Rajamannar Thennati, Akota (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 416 days.

(21) Appl. No.: 10/553,957

(22) PCT Filed: Mar. 4, 2004

(86) PCT No.: PCT/IN2004/000052

§ 371 (c)(1), (2), (4) Date: Oct. 19, 2005

(87) PCT Pub. No.: WO2004/113296

PCT Pub. Date: Dec. 29, 2004

(65) Prior Publication Data

US 2006/0270858 A1   Nov. 30, 2006

(30) Foreign Application Priority Data

Jun. 20, 2003 (IN) .................. 647/MUM/2003
Jul. 17, 2003 (IN) .................. 721/MUM/2003

(51) Int. Cl.
    *C07D 209/82* (2006.01)
(52) U.S. Cl. .............. 548/440; 548/416; 548/427; 548/439; 548/444
(58) Field of Classification Search .............. 548/416, 548/439, 440, 444
    See application file for complete search history.

(56) References Cited

U.S. PATENT DOCUMENTS

| | | | |
|---|---|---|---|
| 4,503,067 A | 3/1985 | Wiedemann et al. | |
| 4,697,022 A | 9/1987 | Leinert | |
| 4,824,963 A | 4/1989 | Leinert | |
| 4,985,454 A | 1/1991 | Leinert | |

FOREIGN PATENT DOCUMENTS

| | | | |
|---|---|---|---|
| EP | 918055 A1 | 5/1999 | |
| IN | 186587 A | 8/1999 | |

*Primary Examiner*—Golam M Shameem
(74) *Attorney, Agent, or Firm*—Westerman, Hattori, Daniels & Adrian, LLP.

(57) ABSTRACT

The present invention provides a process for preparation of 1-[9H-carbazol-4-yloxy]-3-[{2-(2-(methoxy)phenoxy)-ethyl}-amino]-propan-2-ol,a compound of formula 1 in racemic form or in the form of optically active R or S enantiomer or its pharmaceutically acceptable salt, comprising, reacting 4-(oxiranylmethoxy)-9H-carbazole, a compound of formula (2) or the R or S enantiomer thereof with a compound of formula (5), wherein $R_1$ is benzyl or substituted benzyl group, in an aprotic organic solvent in presence of a catalyst to obtain a compound of formula (6), or the R or S enantiomer thereof, wherein $R_1$ is as defined above. The resultant compound of formula (6) is subjected to debenzylation reaction by catalytic hydrogenation to obtain the compound of formula (1), if desired converting the resultant compound of formula (1) to a pharmaceutically acceptable salt thereof.

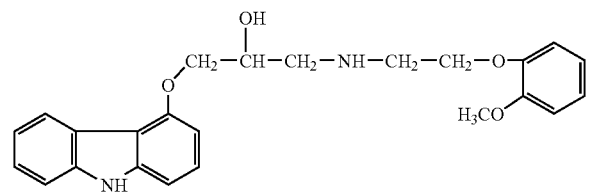

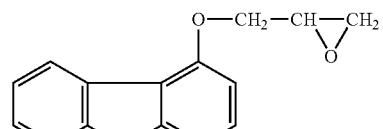

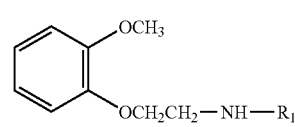

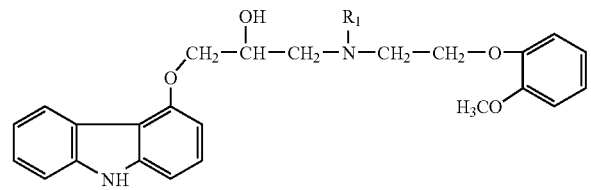

11 Claims, No Drawings

PROCESS FOR PREPARATION OF 1-[9H-CARBAZOL-4-YLOXY]-3-[{2-(2-(-METHOXY)PHENOXY)-ETHYL}-AMINO]-PROPAN-2-OL

The present invention relates to an improved process for preparation of 1-[9H-carbazol-4-yloxy]-3-[{2-(2-(methoxy)phenoxy)-ethyl}-amino]-propan-2-ol.

1-[9H-carbazol-4-yloxy]-3-[{2-(2-(methoxy)phenoxy)-ethyl}-amino]-propan-2-ol, a compound of formula 1, is a well known drug with INN name, carvedilol having antihypertensive effect. Carvedilol is a competitive non-selective β-adrenergic blocking agent with $α_1$-blocking activity.

Formula 1

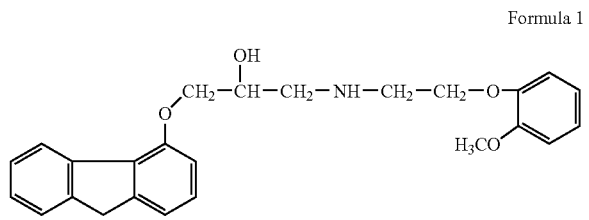

U.S. Pat. No. 4,503,067 (the '067 patent as referred to hereinafter) in example 2 teaches the preparation of 1-[9H-carbazol-4-yloxy]-3-[{2-(2-(methoxy)phenoxy)-ethyl}-amino]-propan-2-ol, a compound of formula 1, (carvedilol) in 39% yield, by reaction of 4-(oxiranylmethoxy)-9H-carbazole, a compound of formula 2 with 2-[2-(methoxy)-phenoxy]-ethylamine, a compound of formula 3.

Formula 2

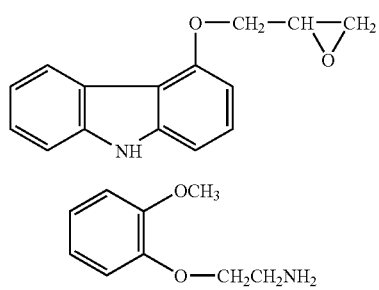

Formula 3

The drawback of the process lies in the fact that along with a compound of formula 1, it also produces a bis-compound of formula 4, Formula 4

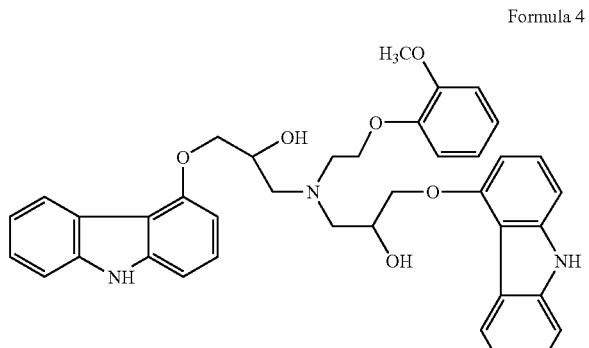

which can not be avoided, making the process uneconomical and unsuitable industrially.

The formation of bis-compound of formula 4 can be avoided by using a secondary amine instead of a primary amine like compound of formula 3. U.S. Pat. No. 4,503,067 in example 5 teaches the preparation of 1-[N-{benzyl}-2-({2-(methoxy)phenoxy)-ethyl}-amino]-3-[9H-carbazol-4-yloxy]-propan-2-ol, a compound of formula 6 (wherein $R_1$ is benzyl, referred to as N-benzyl carvedilol herein), which is the penultimate intermediate for preparation of carvedilol, by reaction of 4-(oxiranylmethoxy)-9H-carbazole, a compound of formula 2 with a secondary amine, viz. N-2-[2-(methoxy)-phenoxy]-ethyl]-benzylamine, a compound of formula 5 (wherein $R_1$ is benzyl), in ethylene glycol dimethyl ether solvent.

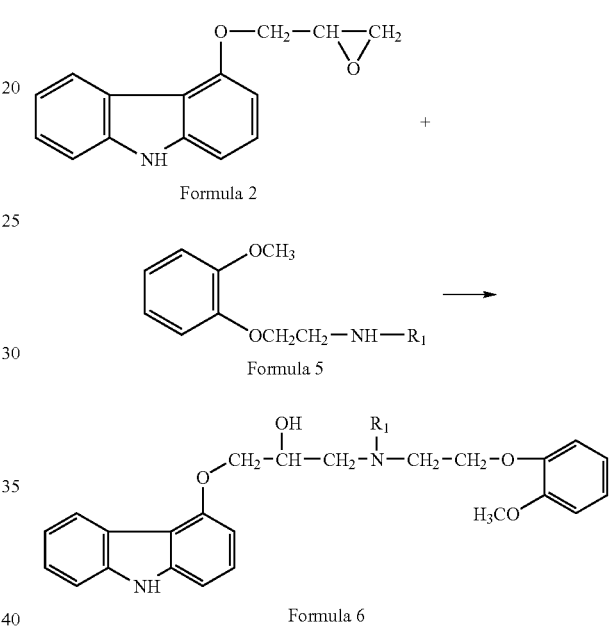

Formula 2

Formula 5

Formula 6

However, the process is not suited to convenient industrial application as it does not provide N-benzyl carvedilol in crystalline form directly from the reaction mixture, but requires isolation of N-benzyl carvedilol by column chromatography.

U.S. Pat. Nos. 4,697,022, 4,824,963 and 4,985,454 relate to R and S enantiomers of N-benzyl carvedilol and carvedilol and to processes for preparation thereof from corresponding enantiomeric compound of formula 2.

European Patent No. 918055B1 (the '055 patent as referred to herein) teaches an improved process for preparation of compound of formula 1 (carvedilol) in racemic or enantiomeric forms prepared via the intermediate compound of formula 6 (N-benzyl carvedilol, wherein $R_1$ is benzyl). The compound of formula 6 is prepared by reaction of 4-(oxiranylmethoxy)-9H-carbazole, a compound of formula 2 with N-2-[2-(methoxy)-phenoxy]-ethyl]-benzylamine, a compound of formula 5 (wherein $R_1$ is benzyl) in a protic organic solvent such as ethanol or isopropanol instead of an aprotic solvent like ethylene glycol dimethyl ether used in the '067 patent. Use of protic organic solvent in place of aprotic solvent obviates column chromatography to isolate the N-benzyl carvedilol in crystalline form by providing the N-benzyl carvedilol in solid form directly from the reaction mixture, which can be isolated and then converted to carvedilol or in-situ converted to carvedilol by subjecting to debenzylation by catalytic hydrogenation. The '055 patent exemplifies in the comparative examples, that preparation of N-benzyl carvedilol by reaction of compound of formula 2 with compound of formula 5 ($R_1$ is benzyl) in an aprotic solvent like ethyl acetate merely provides 3% of the desired N-benzyl carvedilol and when carried out in dioxane solvent only 50% yield is obtained, even after carrying out the reaction for 28 hours at reflux temperature. In contrast, the present invention provides a process wherein the desired compound of formula 6 is prepared in shorter reaction time of about 2 to about 3 hours, using a catalyst with more than about 95% conversion in the same aprotic solvents, that prior art reports to be extremely sluggish.

Further in the '055 patent for preparation of compound of formula 1, starting with 9.6 g of 4-(oxiranylmethoxy)-9H-carbazole, a compound of formula 2, 10.4 g of palladium on carbon (Pd/C) having a 16.2% Pd content and 50% moisture content is used. Thus the ratio of 4-(oxiranylmethoxy)-9H-carbazole to Palladium (Pd) on dried basis is almost 1:0.088 wt/wt.

Indian Patent IN186587, relates to preparation of compound of formula 1, by debenzylation of compound of formula 6, wherein the compound of formula 6 is prepared by reaction of compound of formula 2 with a compound of formula 5, which is exemplified by use of protic solvents like ethanol or isopropanol, the same reaction as disclosed in the prior art '055 patent. Although aprotic solvents such as ethyl acetate are listed in the patent as solvents that may be used, there is no description or example to suggest how the drawbacks of sluggish rate of reaction and low yields under these conditions would be overcome.

The objective of the present invention is to provide a facile process for preparation and purification of compound of formula 1 in racemic or enantiomeric forms.

We have surprisingly found that process for preparation of N-substituted compound represented by a compound of formula 6, by reaction of compound of formula 2 with a compound of formula 5 in an aprotic organic solvent can be accelerated by the use of a catalyst, to provide high yields in shorter time than prior known process. The compound of formula 6 can be converted to carvedilol, a compound of formula 1, by subjecting to debenzylation reaction.

In preferred embodiments of the present invention it is found that the reaction of compound of formula 2 with a compound of formula 5 to obtain a compound of formula 6 and debenzylation of the resultant compound of formula 6 to obtain a compound of formula 1 can be carried out in the same organic aprotic solvent in less time than prior known process for converting compound of formula 2 to compound of formula 6 and then to a compound of formula 1.

In the present invention it is found that the debenzylation of compound of formula 6 can be carried out using significantly lower amount of Pd catalyst than hitherto known.

SUMMARY OF THE PRESENT INVENTION

The present invention provides a process for preparation of 1-[9H-carbazol-4-yloxy]-3-[{2-(2-(methoxy)phenoxy)-ethyl}-amino]-propan-2-ol, a compound of formula 1 in racemic form or in the form of optically active R or S enantiomer or its pharmaceutically acceptable salt,

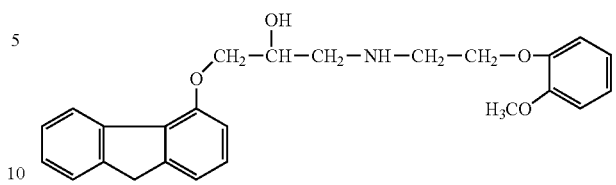

Formula 1 comprising, reacting 4-(oxiranylmethoxy)-9H-carbazole, a compound of formula 2 or the R or S enantiomer thereof with a compound of formula 5,

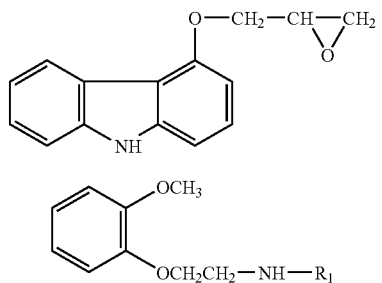

Formula 2

Formula 5 wherein $R_1$ is benzyl or substituted benzyl group, in an aprotic organic solvent in presence of a catalyst to obtain a compound of formula 6, or the R or S enantiomer thereof, wherein $R_1$ is as defined above.

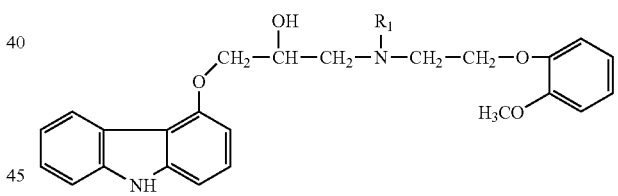

Formula 6

The resultant compound of formula 6 is subjected to debenzylation reaction by catalytic hydrogenation to obtain the compound of formula 1, if desired converting the resultant compound of formula 1 to a pharmaceutically acceptable salt thereof.

DETAILED DESCRIPTION OF THE INVENTION

The present invention provides a facile process for preparation of compound of formula 1 (carvedilol) or R or S enantiomer thereof by reaction of compound of formula 2 or R or S enantiomer thereof with a compound of formula 5 ($R_1$ is benzyl or substituted benzyl group) in an aprotic organic solvent in presence of a catalyst to form a compound of formula 6 or R or S enantiomer thereof ($R_1$ is benzyl or substituted benzyl group), the compound of formula 6 or R or S enantiomer thereof is converted to the compound of formula 1 or R or S enantiomer thereof by subjecting it to debenzylation reaction. Examples of substituted benzyl group are phenyl ring of the benzyl group substituted with one or more halogen, alkoxy or haloalkoxy group such as —OCF$_3$ group and the like.

In a preferred embodiment of the present invention the reaction of compound of formula 2 or R or S enantiomer thereof, with a compound of formula 5 (wherein R$_1$ is benzyl) to obtain 1-[N-{benzyl}-2-({2-(methoxy)phenoxy)-ethyl}-amino]-3-[9H-carbazol-4-yloxy]-propan-2-ol, a compound of formula 6 (N-benzyl carvedilol, wherein R$_1$ is benzyl) or R or S enantiomer thereof is carried out in an aprotic organic solvent in presence of a catalyst.

As referred to herein the term 'compound of formula 1' includes the racemic or enantiomeric form thereof, the term 'compound of formula 2' includes the racemic or enantiomeric form thereof and the term 'compound of formula 6' includes the racemic or enantiomeric form thereof unless specified otherwise.

The aprotic organic solvent like ethers, esters, ketones, amides, nitriles, hydrocarbons, halogenated hydrocarbons, aromatic solvents or mixtures thereof can be used in the process of the present invention. Preferably ethers, esters or amide solvents; more preferably ether or ester solvents may be used. Examples of ethers are cyclic ethers such as dioxane, tetrahydrofuran and the like, acyclic ethers such as dimethoxyethane, disopropylether, methyl-tertbutylether and the like. Examples of ester solvents are ethylacetate, methylacetate and the like.

The catalyst can be an organic acid such as mono or polycarboxylic acids like acetic acid, oxalic acid, citric acid, glutaric acid, succinic acid and the like; a halocarboxylic acid such as trifluroacetic acid and the like; a substituted or unsubstituted aromatic or heteroaromatic carboxylic acid such as benzoic acid, nicotinic acid and the like; a sulphonic acid such as methanesulphonic acid, benzenesulphonic acid, para-toluenesulphonic acid and the like; a Lewis acid such as a halide salt of zinc, boron, copper, iron, nickel, cobalt, tin, aluminum, antimony and the like for example, $ZnCl_2$, $AlCl_3$, $CoCl_2$, $CuCl_2$, alkali or alkaline earth metal salts such as lithium or magnesium halides and the like, perchlorate salts for example, lithium perchlorate, copper perchlorate and the like; zinc acetate, zinc oxide, $BF_3$ etherate, zinc salt of 2-ethylhexanoic acid; an inorganic acid such as hydrochloric acid, hydrobromic acid, sulphuric acid, phosphoric acid, polyphosphoric acid, sodium dihydrogen phosphate and the like or water.

In a preferred embodiment the aprotic organic solvent for carrying out the process of the present invention may be selected from ethyl acetate, dimethoxyethane and dioxane and the catalyst may be selected from $ZnCl_2$, $AlCl_3$, $CoCl_2$, $CuCl_2$, acetic acid, trifluoroacetic acid, succinic acid, glutaric acid, oxalic acid, zinc acetate, sodium dihydrogen phosphate and water.

In a particularly preferred embodiment of the process of the present invention the aprotic organic solvent may be selected from ethyl acetate, dimethoxyethane and dioxane and the catalyst may be selected from $ZnCl_2$, acetic acid and trifluoroacetic acid.

In another particularly preferred embodiment of the process of the present invention the aprotic organic solvent may be selected from ethyl acetate, dimethoxyethane and dioxane and the catalyst is $ZnCl_2$.

In preferred embodiments of the present invention the aprotic organic solvent and the catalyst used together include ethyl acetate and $ZnCl_2$, dimethoxyethane and $ZnCl_2$, dioxane and $ZnCl_2$, ethyl acetate and acetic acid, dimethoxyethane and acetic acid, dioxane and acetic acid, ethyl acetate and trifluoroacetic acid, dimethoxyethane and trifluoroacetic acid, dioxane and trifluoroacetic acid.

Preferably, the mole ratio of the compound of formula 2: $ZnCl_2$ may be in the range of 1:0.1 to 1:0.4, preferably 1:0.36; the mole ratio of the compound of formula 2:acetic acid may be in the range of 1:0.15 to 1:0.75, preferably 1:0.6; the mole ratio of the compound of formula 2: trifluoroacetic acid may be in the range of 1:0.15 to 1:0.75, preferably 1:0.6.

In a particular embodiment of the present invention the reaction of 4-(oxiranylmethoxy)-9H-carbazole or R or S enantiomer thereof, a compound of formula 2, with N-2-[2-(methoxy)-phenoxy]-ethyl]-benzylamine, a compound of formula 5 (wherein R$_1$ is benzyl) to obtain 1-[N-{benzyl}-2-({2-(methoxy)phenoxy)-ethyl}-amino]-3-[9H-carbazol-4-yloxy]-propan-2-ol, a compound of formula 6 (N-benzyl carvedilol, wherein R$_1$ is benzyl) or R or S enantiomer thereof is carried out in an aprotic organic solvent in presence of a catalyst.

In one preferred embodiment of the present invention the reaction of compound of formula 2 with a compound of formula 5 to obtain a compound of formula 6 and debenzylation of the resultant compound of formula 6 to obtain a compound of formula 1 can be carried out in the same organic aprotic solvent. More preferably, in step 'a' of the process the aprotic organic solvent used is ethyl acetate and in step 'b' of the process the debenzylation reaction is carried out in ethyl acetate in presence of Pd/C catalyst.

If desired, the reaction of a compound of formula 2 with a compound of formula 5 in an aprotic organic solvent in presence of a catalyst to obtain a compound of formula 6 may be carried out in one solvent and the subsequent denbenzylation of compound of formula 6 to obtain compound of formula 1 may be carried out in another solvent.

In the process of the present invention, the reaction of compound of formula 2 with the compound of formula 5 in an aprotic organic solvent in presence of a catalyst can be carried out between the temperature range of 30° C. to 100° C., preferably 60° C. to 80° C.

Whereas the reaction in aprotic solvent such as ethyl acetate or dioxane in the absence of a catalyst is reported to be sluggish providing about 3% conversion to desired N-benzyl carvedilol in ethyl acetate and presence of about 50% unreacted starting compound in dioxane after about 28 hours, according to the present invention high yields of compound of formula 6 are obtained when the reaction is carried out for a period of about 0.5 to about 60 hours, preferably about 2 to about 48 hours. More preferred embodiments the process provides high yields in about 0.5 to about 3 hours.

In a particularly preferred embodiment the reaction of compound of formula 2 with compound of formula 5 is carried out in ethyl acetate in presence of catalytic $ZnCl_2$, to obtain the compound of formula 6, the resultant compound of formula 6 is further subjected to debenzylation by catalytic hydrogenation carried out in ethyl acetate.

The present invention provides a process for preparation and purification of compound of formula 1 wherein the debenzylation step is carried out using significantly lower amount of Pd/C catalyst.

In the '055 patent for 9.6 g of 4-(oxiranylmethoxy)-9H-carbazole, a compound of formula 2, 10.4 g of palladium on carbon (Pd/C) is used in the debenzylation step, which is having 16.2% Pd content and 50% moisture content. Thus the ratio of 4-(oxiranylmethoxy)-9H-carbazole to palladium (Pd) on dried basis is almost 1:0.088 wt/wt.

In contrast, the debenzylation step in the process of the present invention can be carried out with significantly lower amount of Pd catalyst loading. For example, for 100 g of 4-(oxiranylmethoxy)-9H-carbazole, a compound of formula 2, only 14 g of palladium on carbon (Pd/C) with 5% Pd content and 50% moisture content is effective in carrying out the debenzylation step. Thus in the process of the present invention, the ratio of 4-(oxiranylmethoxy)-9H-carbazole to palladium (Pd) on dried basis of 1:0.0035 wt/wt can be effectively used.

Although not wishing to be bound by theories, the use of less amount of Pd/C catalyst in debenzylation step in the process of the present invention can be attributed to use of solvent like ethyl acetate. N-benzyl carvedilol, a compound of formula 6 ($R_1$ is benzyl), which is a viscous low melting solid, being highly miscible in ethyl acetate, when ethyl acetate solution of compound of formula 6 is subjected to debenzylation reaction in presence of Pd/C catalyst, the Pd/C surface is more readily available for the hydrogenation process. Hence the reaction rate is rapid and poisoning of Pd/C is prevented. Even the high solubility of carvedilol is advantageous in allowing the Pd/C catalyst to function efficiently.

The use of protic solvent like an alcohol as in the '055 patent, for the preparation of N-benzyl carvedilol, results in a reaction system wherein N-benzyl carvedilol is partially miscible because of its viscous oily nature, resulting in Pd/C catalyst surface not being readily accessible for hydrogentaion process, thus poisoning the catalyst in turn, which could be the reason for higher loading of Pd/C catalyst used in this prior art process.

In a preferred embodiment of the present invention, the aprotic organic solvent for step 'a' of the process is ethyl acetate and the debenzylation reaction is carried out in presence of Pd/C catalyst, characterized in that the ratio of 4-(oxiranylmethoxy)-9H-carbazole:palladium (Pd) on dried basis is between the range of 1:0.001 to 1:0.005 wt/wt.

In a preferred embodiment of the process of the present invention, the aprotic organic solvent for step 'a' of the process is ethyl acetate and the debenzylation reaction is carried out in presence of Pd/C catalyst in ethyl acetate, characterized in that the ratio of 4-(oxiranylmethoxy)-9H-carbazole:Pd on dried basis is 1:0.0035 wt/wt.

We have also observed that the debenzylation reaction rate is faster when the reaction mass that is subjected to debenzylation contains an acid source like acetic acid. Thus in a preferred embodiment of the process the debenzylation reaction is carried out in presence of an acid such as acetic acid that can protonate the primary amine by-product, thereby preventing poisoning of the Pd catalyst.

Although not wishing to be bound by theories it could be reasoned that any unreacted compound of formula 5 for e.g. N-2-[2-(methoxy)-phenoxy]-ethyl]-benzylamine (compound of formula 5, $R_1$ is benzyl), would get converted to 2-[2-(methoxy)-phenoxy]-ethylamine, a compound of formula 3, a primary amine, in step 'b' of the process. This primary amine by-product could poison the catalyst, however in the presence of a compound like acetic acid, this primary amine by-product would get protonated and thus prevent poisoning of the Pd catalyst.

Accordingly the Pd/C catalyst can be recycled in the process of the present invention in step 'b', after checking the activity of the catalyst by standard analytical procedures known in the art.

In the process of the present invention the debenzylation reaction is carried out at temperature between the range of about 50° C. to about 75° C. In the process of the present invention the debenzylation reaction is carried out for a period of about 3 hours to about 12 hours. In a preferred embodiment the debenzylation reaction is carried out at temperature between the range of about 60° C. to about 75° C. for a period of about 8 hours to about 10 hours. In the process of the present invention the debenzylation reaction may be carried out at hydrogen pressure between, 0.1 to 5 Kg/cm$^2$, preferably 3.5 to 4.5 Kg/cm$^2$.

In a preferred embodiment the present invention provides a process for preparation of 1-[9H-carbazol-4-yloxy]-3-[{2-(2-(methoxy)phenoxy)-ethyl}-amino]-propan-2-ol, a compound of formula 1 in racemic form or in the form of optically active R or S-enantiomer or its pharmaceutically acceptable salt, Formula 1

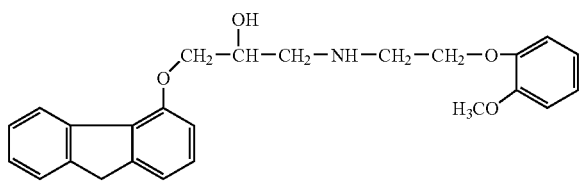

comprising subjecting the compound of formula 6 or the R or S enantiomer thereof, Formula 6

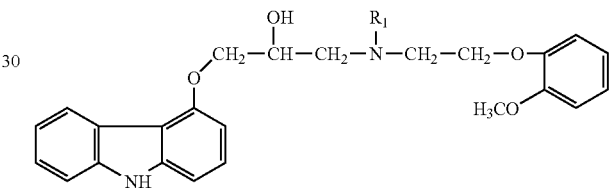

wherein $R_1$ is benzyl or substituted benzyl group, to debenzylation reaction by catalytic hydrogenation in ethyl acetate, if desired converting the resultant compound of formula 1 to a pharmaceutically acceptable salt thereof.

In a preferred embodiment a compound of formula 6 wherein $R_1$ is benzyl is subjected to debenzylation reaction in ethyl acetate to obtain a compound of formula 1.

In more preferred embodiment a compound of formula 6 is subjected to debenzylation reaction in ethyl acetate in presence of an acid such as acetic acid to obtain a compound of formula 1.

The following examples are given by way of illustration only and not to be construed as limiting.

EXAMPLES

Example 1

To 400 ml ethylacetate, 70 g (0.27 moles) of anhydrous N-2-[2-(methoxy)-phenoxy]-ethyl]-benzylamine, 10.25 g (0.075 moles) of anhydrous ZnCl$_2$ and 50 g (0.21 moles) of 4-(oxiranylmethoxy)-9H-carbazole are added and the reaction mixture is heated to 70-75° C. for 3 hrs (TLC control for checking conversion to N-benzylcarvedilol). The reaction mixture is cooled to ambient temperature and quenched into 100 ml of ~12-15% aqueous ammonia. The aqueous layer separated, and the product enriched organic layer is washed with water till neutral pH. The organic layer is charcoalised, filtered. To this solution of N-benzyl carvedilol in ethylacetate, (7 g) of wet Pd/C catalyst (5% Pd content and 50% moisture content) is added. The reaction mixture is hydrogenated at 3.5-4.5 Kg/cm$^2$ at temperature of 60-70° C. for a period of about 10 hours. The reaction mixture is filtered and filtrate concentrated to remove ethylacetate. To the resultant syrupy mass n-butanol (100 ml) is added and the solution is stirred for about 10 hours, the crystals separated by filtration, washed successively with n-butanol (50 ml) and toluene (50 ml) to obtain carvedilol (47 g). The product is recrystallized from 3 volumes of ethyl acetate to obtain carvedilol (42 g).

Example 2

To 250 ml dimethoxyethane, 70 g (0.27 moles) of anhydrous N-2-[2-(methoxy)-phenoxy]-ethyl]-benzylamine, 10.25 g (0.075 moles) of anhydrous ZnCl$_2$ and 50 g (0.21 moles) of 4-(oxiranylmethoxy)-9H-carbazole are added and the reaction mixture is heated to 70-75° C. for 2.5 hrs (TLC control for checking conversion to N-benzyl carvedilol). Dimethoxyethane is distilled off from the reaction mixture and to the concentrated mass is added 400 ml ethylacetate, followed by 100 ml of ~12-15% aqueous ammonia. The aqueous layer separated, and the product enriched organic layer is washed with water till neutral pH. The organic layer is charcoalised, filtered. To this solution of N-benzyl carvedilol in ethylacetate, (7 g) of wet Pd/C catalyst (5% Pd content and 50% moisture content) is added. The reaction mixture is hydrogenated at 3.5-4.5 Kg/cm$^2$ at temperature of 60-70° C. for a period of about 10 hours. The reaction mixture is filtered and filtrate concentrated to remove ethylacetate. To the resultant syrupy mass n-butanol (100 ml) is added and the solution is stirred for about 10 hours, the crystals separated by filtration, washed successively with n-butanol (50 ml) and toluene (50 ml) to obtain carvedilol (50 g). The product is recrystallized from 3 volumes of ethyl acetate to obtain carvedilol (45 g).

Example 3

To 5 ml Dioxane 1.4 g (0.0054 moles) of anhydrous N-2-[2-(methoxy)-phenoxy]-ethyl]-benzylamine, 0.21 g (0.0015 moles) of anhydrous ZnCl$_2$ and 1 g (0.0042 moles) of 4-(oxiranylmethoxy)-9H-carbazole are added and the reaction mixture is heated to 70-75° C. for 2.5 hrs (TLC control for checking conversion to N-benzyl carvedilol). The dioxane is distilled off from the reaction mixture and to the concentrated mass is added 10 ml ethylacetate, followed by 2 ml of ~12-15% aqueous ammonia. The aqueous layer separated, and the product enriched organic layer is washed with water till neutral pH. The organic layer is charcoalised, filtered. To this solution of N-benzyl carvedilol in ethylacetate, (0.14 g) of wet Pd/C catalyst (5% Pd content and 50% moisture content) is added. The reaction mixture is hydrogenated at 3.5-4.5 Kg/cm$^2$ at temperature of 60-70° C. for a period of about 10 hours. The reaction mixture is filtered and filtrate concentrated to remove ethylacetate. To the resultant syrupy mass n-butanol (2 ml) is added and the solution is stirred for about 10 hours, the crystals separated by filtration, washed successively with n-butanol (1 ml) and toluene (1 ml) to obtain carvedilol (0.9 g). The product is recrystallized from 3 volumes of ethyl acetate to obtain carvedilol (0.8 g).

Example 4

To 450 ml ethylacetate, 70 g (0.27 moles) of anhydrous N-2-[2-(methoxy)-phenoxy]-ethyl]-benzylamine, 3.65 g (0.06 moles) of acetic acid and 25 g (0.105 moles) of 4-(oxiranylmethoxy)-9H-carbazole are added and the reaction mixture is heated to reflux for 24 hrs (TLC control for checking conversion to N-benzyl carvedilol). To the above reaction mixture, a second lot of 3.65 g (0.06 moles) of acetic acid and 25 g (0.105 moles) of 4-(oxiranylmethoxy)-9H-carbazole are added and the reaction mixture is further heated to reflux for 24 hrs (TLC control for checking conversion to N-benzyl carvedilol). The reaction mixture is cooled to ambient temperature and subjected to hydrogenation reaction. To this solution of N-benzyl carvedilol in ethylacetate, (7 g) of wet Pd/C catalyst (5% Pd content and 50% moisture content) is added. The reaction mixture is hydrogenated at 3.5-4.5 Kg/cm$^2$ at temperature of 60-70° C. for a period of about 8 hours. The reaction mixture is filtered and the filtrate is washed with 12-15% v/v aqueous ammonia (1 volume w. r .t. to the carbazole). The product enriched organic layer is separated and concentrated to remove ethylacetate. To the resultant syrupy mass n-butanol (100 ml) is added and the solution is stirred for about 10 hours, the crystals separated by filtration, washed successively with n-butanol (50 ml) and toluene (50 ml) to obtain carvedilol (45 g). The product is recrystallized from 3 volumes of ethyl acetate to obtain carvedilol (41 g).

Example 5

To 5 ml dimethoxyethane, 1.4 g (0.0054 moles) of anhydrous N-2-[2-(methoxy)-phenoxy]-ethyl]-benzylamine, 0.07 g (0.00125 moles) of acetic acid and 0.5 g (0.0021 moles) 4-(oxiranylmethoxy)-9H-carbazole are added and the reaction mixture is heated to 70-75° C. for 24 hrs (TLC control for checking conversion to N-benzyl carvedilol). To this reaction mixture, a second lot of 0.07 g (0.00125 moles) of acetic acid and 0.5 g (0.0021 moles) of 4-(oxiranylmethoxy)-9H-carbazole are added and the reaction mixture is further heated to 0-75° C. for 24 hrs (TLC control for checking conversion of to N-benzyl carvedilol). Dimethoxyethane is distilled off from the reaction mixture and to the concentrated reaction mixture 10 ml ethylacetate is added and subjected the reaction mass to hydrogenation. To this solution of N-benzyl carvedilol in ethylacetate, (0.14 g) of wet Pd/C catalyst (5% Pd content and 50% moisture content) is added. The reaction mixture is hydrogenated at 3.5-4.5 Kg/cm$^2$ at temperature of 60-70° C. for a period of about 8 hours. The reaction mixture is filtered and the filtrate is washed with 12-15% v/v aqueous ammonia (1 volume w. r .t. to the carbazole). The product enriched organic layer is separated and concentrated to remove ethylacetate. To the resultant syrupy mass n-butanol (2 ml) is added and the solution is stirred for about 10 hours, the crystals separated by filtration, washed successively with n-butanol (1 ml) and toluene (1 ml) to obtain carvedilol (0.9 g). The product is recrystallized from 3 volumes of ethyl acetate to obtain carvedilol (0.75 g).

Example 6

To 5 ml dioxane 1.4 g (0.0054 moles) of anhydrous N-2-[2-(methoxy)-phenoxy]-ethyl]-benzylamine, 0.07 g (0.00125 moles) of acetic acid and 0.5 g (0.0021 moles) of 4-(oxiranylmethoxy)-9H-carbazole are added and the reaction mixture is heated to 70-75° C. for 24 hrs (TLC control for checking conversion to N-benzyl carvedilol). To this reaction mixture, a second lot of 0.07 g (0.00125 moles) of acetic acid and 0.5 g (0.0021 moles) of 4-(oxiranylmethoxy)-9H-carbazole are added and the reaction mixture is further heated to 70-75° C. for 24 hrs (TLC control for checking conversion to N-benzyl carvedilol). Dioxane is distilled off from the reaction mixture and to the concentrated reaction mixture 10 ml ethylacetate is added and subjected the reaction mass to hydrogenation. To this solution of N-benzyl carvedilol in ethylacetate, (0.14 g) of wet Pd/C catalyst (5% Pd content and 50% moisture content) is added. The reaction mixture is hydrogenated at 3.5-4.5 Kg/cm$^2$ at temperature of 60-70° C. for a period of about 8 hours. The reaction mixture is filtered and the filtrate is washed with 12-15% v/v aqueous ammonia (1 volume w. r .t. to the carbazole). The product enriched organic layer is separated and concentrated to remove ethylacetate. To the resultant syrupy mass n-butanol (2 ml) is added and the solution is stirred for about 10 hours, the crystals separated by filtration, washed successively with n-butanol (1 ml) and toluene (1 ml) to obtain carvedilol (0.9 g). The product is recrystallized from 3 volumes of ethyl acetate to obtain carvedilol (0.75 g).

Example 7

To 8 ml ethylacetate 1.4 g (0.0054 moles) of anhydrous N-2-[2-(methoxy)-phenoxy]-ethyl]-benzylamine, 0.15 g (0.0013 moles) trifluoroacetic acid and 0.5 g (0.0021 moles) of 4-(oxiranylmethoxy)-9H-carbazole are added and the reaction mixture is heated to 70-75° C. for 24 hrs (TLC control for checking conversion to N-benzyl carvedilol). To this reaction mixture, a second lot of 0.15 g (0.0013 moles) of trifluoroacetic acid and 0.5 g (0.0021 moles) of 4-(oxiranylmethoxy)-9H-carbazole are added and the reaction mixture is further heated to 70-75° C. for 24 hrs (TLC control for checking conversion to N-benzyl carvedilol). The reaction mixture can be further subjected to hydrogenation reaction as described above in example 4.

Example 8

To 5 ml dimethoxyethane 1.4 g (0.0054 moles) of anhydrous N-2-[2-(methoxy)-phenoxy]-ethyl)-benzylamine, 0.15 g (0.0013 moles) of trifluoroacetic acid and 0.5 g (0.0021 moles) of 4-(oxiranylmethoxy)-9H-carbazole are added and the reaction mixture is heated to 70-75° C. for 24 hrs (TLC control for checking conversion to N-benzyl carvedilol). To this reaction mixture, a second lot of 0.15 g (0.0013 moles) of trifluoroacetic acid and 0.5 g (0.0021 moles) of 4-(oxiranylmethoxy)-9H-carbazole are added and the reaction mixture is further heated to 70-75° C. for 24 hrs (TLC control for checking conversion to N-benzyl carvedilol). The reaction mixture can be further subjected to hydrogenation reaction after distilling off dimethoxyethane and adding 10 ml ethylacetate, as described above in example 5.

Example 9

To 5 ml dioxane 1.4 g (0.0054 moles) of anhydrous N-2-[2-(methoxy)-phenoxy]-ethyl]-benzylamine, 0.15 g (0.0013 moles) of trifluoroacetic acid and 0.5 g (0.0021 moles) of 4-(oxiranylmethoxy)-9H-carbazole are added and the reaction mixture is heated to 70-75° C. for 24 hrs (TLC control for checking conversion to N-benzyl carvedilol). To this reaction mixture, a second lot of 0.15 g (0.0013 moles) of trifluoroacetic acid and 0.5 g (0.0021 moles) of 4-(oxiranylmethoxy)-9H-carbazole are added and the reaction mixture is further heated to 70-75° C. for 24 hrs (TLC control for checking conversion to N-benzyl carvedilol). The reaction mixture can be further subjected to hydrogenation reaction as described above in example 6, after distilling off dioxane and adding 10 ml ethylacetate.

Example 10

To 400 ml ethylacetate, 70 g (0.27 moles) anhydrous N-2-[2-(methoxy)-phenoxy]-ethyl]-benzylamine, 10.25 g (0.075 moles) of anhydrous ZnCl$_2$ and 50 g (0.21 moles) of 4-(oxiranylmethoxy)-9H-carbazole are added and the reaction mixture is heated to 70-75° C. for 3 hrs (TLC control for checking conversion to N-benzyl carvedilol). The reaction mixture is cooled to ambient temperature and quenched into 100 ml of ~12-15% aqueous ammonia. The aqueous layer separated, and the product enriched organic layer is washed with water till neutral pH. The organic layer is charcoalised, filtered and the filtrate subjected to hydrogenation reaction. To this solution of N-benzyl carvedilol in ethylacetate, (7 g) of wet Pd/C catalyst (5% Pd content and 50% moisture content) is added. The reaction mixture is hydrogenated at 4.0 Kg/cm$^2$ at temperature of 60-70° C. for a period of about 10 hours. The reaction mixture is filtered and filtrate concentrated to about 3-4 volumes of the original volume and left for crystallisation of crude carvedilol for a period of about 10 hrs and filtered to obtain carvedilol (50 g). The product is recrystallized from 3 volumes of ethyl acetate to obtain carvedilol (42 g).

Example 11

To 400 ml ethylacetate, 70 g (0.27 moles) anhydrous N-2-[2-(methoxy)-phenoxy]-ethyl]-benzylamine, 10.25 g (0.075 moles) of anhydrous ZnCl$_2$ and 50 g (0.21 moles) of 4-(oxiranylmethoxy)-9H-carbazole are added and the reaction mixture is heated to 70-75° C. for 3 hrs (TLC control for checking conversion to N-benzyl carvedilol). The reaction mixture is cooled to ambient temperature and quenched into 100 ml of ~12-15% aqueous ammonia. The aqueous layer separated, and the product enriched organic layer is washed with water till neutral pH. The organic layer is charcoalised, filtered and the filtrate subjected to hydrogenation reaction. To this solution of N-benzyl carvedilol in ethylacetate, 5 ml acetic acid is added, followed by (7 g) of wet Pd/C catalyst (5% Pd content and 50% moisture content) is added. The reaction mixture is hydrogenated at 4.0 Kg/cm$^2$ at temperature of 60-70° C. for a period of about 8 hours. The reaction mixture is filtered and the filtrate is washed with 40 ml of 12-15% v/v aqueous ammonia. The product enriched organic layer is separated and concentrated to remove ethylacetate. To the resultant syrupy mass n-butanol (100 ml) is added and the solution is stirred for about 10 hours, the crystals separated by filtration, washed successively with n-butanol (50 ml) and toluene (100 ml) to obtain carvedilol (55.4 g). The product is recrystallized from 3 volumes of ethyl acetate to obtain carvedilol (49 g).

Example 12

To 450 ml ethylacetate, 82.5 g (0.27 moles, on dry basis) of N-2-[2-(methoxy)-phenoxy]-ethyl]-benzylamine (moisture content 15%), 3.65 g (0.06 moles) of acetic acid and 25 g (0.105 moles) of 4-(oxiranylmethoxy)-9H-carbazole are added and the reaction mixture is heated to reflux for 24 hrs (TLC control for checking conversion of to N-benzyl carvedilol). To the above reaction mixture, a second lot of 3.65 g (0.06 moles) of acetic acid and 25 g (0.105 moles) of 4-(oxiranylmethoxy)-9H-carbazole are added and the reaction mixture is further heated to reflux for 24 hrs (TLC control for checking conversion to N-benzyl carvedilol). The reaction mixture is cooled to ambient temperature and subjected to hydrogenation reaction as described in example 4 above.

Example 13

To 400 ml dioxane, 80.6 g (0.31 moles) of N-2-[2-(methoxy)-phenoxy]-ethyl]-benzylamine (moisture content 15%), 25 ml Water and 25 g (0.105 moles) of 4-(oxiranylmethoxy)-9H-carbazole are added and the reaction mixture is heated to 78-80° C. for 24 hrs (TLC control for checking conversion to N-benzyl carvedilol). To this reaction mixture, a second lot of 25 ml Water and 25 g (0.105 moles) of 4-(oxiranylmethoxy)-9H-carbazole are added and the reaction mixture is further heated to 78-80° C. for 7 hrs (TLC control for checking conversion to N-benzyl carvedilol). The reaction mixture can be further subjected to hydrogenation reaction as described in example 6, after distilling off dioxane and adding ethylacetate.

We claim:

1. A process for preparation of 1-[9H-carbazol-4-yloxy]-3-[{2-(2-(methoxy)phenoxy)-ethyl}-amino]-propan-2-ol, a compound of formula 1 in racemic form or in the form of optically active R or S enantiomer or its pharmaceutically acceptable salt,

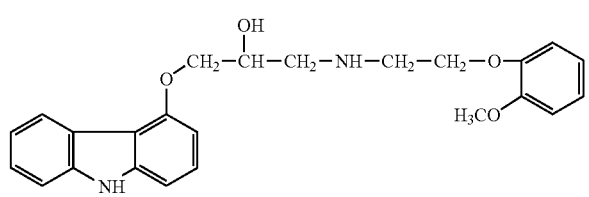

Formula 1 comprising,
a) reacting 4-(oxiranylmethoxy)-9H-carbazole, a compound of formula 2 or the R or S enantiomer thereof with a compound of formula 5,

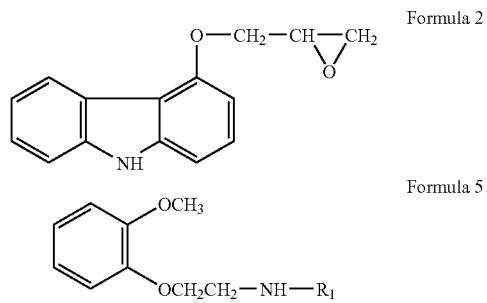

Formula 2

Formula 5 wherein $R_1$ is benzyl or substituted benzyl group, in an aprotic organic solvent in presence of a catalyst to obtain a compound of formula 6, or the R or S enantiomer thereof, wherein $R_1$ is as defined above,

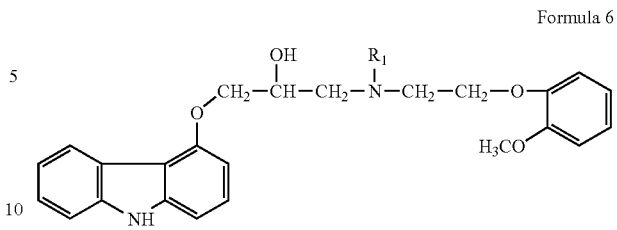

Formula 6 b) subjecting the resultant compound of formula 6 to debenzylation reaction by catalytic hydrogenation to obtain the compound of formula 1, if desired converting the resultant compound of formula 1 to a pharmaceutically acceptable salt thereof.

2. The process as claimed in claim 1 comprising,
a) reacting a compound of formula 2 with N-2-[2-(methoxy)-phenoxy]-ethyl]-benzylamine, a compound of formula 5 wherein $R_1$ is benzyl to obtain 1-[N-{benzyl}-2-({2-(methoxy)phenoxy)-ethyl}-amino]-3- [9H-carbazol-4-yloxy]-propan-2-ol, a compound of formula 6 wherein $R_1$ is benzyl.

3. The process as claimed in claim 1, wherein the aprotic organic solvent is selected from ethyl acetate, dioxane, dimethoxyethane and the catalyst is selected from $ZnCl_2$, $AlCl_3$, $CoCl_2$, $CuCl_2$, acetic acid, trifluoroacetic acid, succinic acid, glutaric acid, oxalic acid, zinc acetate, sodium dihydrogen phosphate and water.

4. The process as claimed in claim 1, wherein the aprotic organic solvent is selected from ethyl acetate, dioxane, dimethoxyethane and the catalyst is selected from $ZnCl_2$, acetic acid, trifluoroacetic acid.

5. The process as claimed in claim 1, wherein the catalyst is $ZnCl_2$.

6. The process as claimed in claim 1, wherein, in step 'a' of the process the aprotic organic solvent is ethyl acetate and in step 'b' of the process the debenzylation reaction is carried out in ethyl acetate in presence of Pd/C catalyst.

7. The process as claimed in claim 6, wherein the debenzylation reaction is carried out in ethyl acetate in presence of acetic acid.

8. The process as claimed in claim 6, wherein the debenzylation reaction is carried out in presence of Pd/C catalyst, wherein the ratio of the compound of formula 2:Palladium (Pd) on dried basis is between the range of 1:0.001 to 1:0.005 wt/wt.

9. The process as claimed in claim 8, wherein the ratio is 1:0.0035 wt/wt.

10. The process as claimed in claim 1, wherein the catalyst of step (a) is selected from $ZnCl_2$, $AlCl_3$, $CoCl_2$, $CuCl_2$, acetic acid, trifluoroacetic acid, succinic acid, glutaric acid, oxalic acid, zinc acetate, sodium dihydrogen phosphate and water.

11. The process as claimed in claim 1, wherein the catalyst of step (a) is selected from $ZnCl_2$, acetic acid, trifluoroacetic acid.

* * * * *